US007266407B2

(12) United States Patent
Li et al.

(10) Patent No.: US 7,266,407 B2
(45) Date of Patent: Sep. 4, 2007

(54) MULTI-FREQUENCY MICROWAVE-INDUCED THERMOACOUSTIC IMAGING OF BIOLOGICAL TISSUE

(75) Inventors: Jian Li, Gainesville, FL (US); Gang Wang, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 197 days.

(21) Appl. No.: 10/714,795

(22) Filed: Nov. 17, 2003

(65) Prior Publication Data

US 2005/0107692 A1 May 19, 2005

(51) Int. Cl.
*A61B 5/05* (2006.01)
(52) U.S. Cl. .................................... 600/430
(58) Field of Classification Search ................ 600/430
See application file for complete search history.

(56) References Cited

U.S. PATENT DOCUMENTS

| 4,641,659 | A | * | 2/1987 | Sepponen ................... 600/430 |
| 5,630,154 | A | * | 5/1997 | Bolstad et al. ................. 712/19 |
| 6,031,862 | A | | 2/2000 | Fullerton |
| 6,104,942 | A | | 8/2000 | Kruger et al. |
| 6,236,862 | B1 | * | 5/2001 | Erten et al. .................. 455/501 |
| 6,567,688 | B1 | | 5/2003 | Wang |
| 2003/0088180 | A1 | * | 5/2003 | Van Veen et al. ........... 600/430 |
| 2004/0167399 | A1 | * | 8/2004 | Li ............................... 600/430 |

OTHER PUBLICATIONS

Sun et al., "Time-frequency analysis for plastic landmine detection via forward-looking ground penetrating radar," IEE Proc.-Radar Sonar Navig., 150:253-261, 2003.
Li et al., "Target Detection with Synthetic Aperture Radar," IEEE Transactions on Aerospace and Electronic Systems, 32:613-627, 1996.
Daniels, D., "An overview of RF sensors for mine detection: Part 3 Radar," http://demining.jrc.it/aris/events/mine99/program/P41-47/MINE-RAD.htm, 1-9, Mar. 17, 2004.
De Jongh et al., "Design and analysis of new GPR antenna concepts," Delft University of Technology, Faculty of Information Technology and Systems International Research Centre for Telecommunications-transmission and Radar(IRCTR), date is not available.
Buchenauer et al., "Aperture Efficiencies of Impluse Radiating Antennas," Air Force Research Laboratory/DEHP, 91-108, 1999.
Stoica et al., "Robust Capon Beamforming," IEEE Signal Processing Letters, 10:172-175, 2003.
Yermakov, G., "The Exact Solution of the Problem of Ultra Wideband Signals Radiation by a TEM-Horn," DIPED-2002 Proceedings, 42-45.
Liu et al., "Pulse Radiation Antenna Feeded With a Face-to-Face TEM Horn," IEEE, 447-450, 2000.
Li et al., "On Robust Capon Beamforming and Diagonal Loading," IEEE Transactions on Signal Processing, 51:1702-1715, 2003.
Li et al., "A Confocal Microwave Imaging Algorithm for Breast Cancer Detection," IEEE Microwave and Wireless Components Letters, 11:130-132, 2001.
Fear et al., "Enhancing Breast Tumor Detection with Near-Field Imaging," IEEE Microwave Magazine, 48-56, 2002.

(Continued)

*Primary Examiner*—Brian L. Casler
*Assistant Examiner*—John F. Ramirez
(74) *Attorney, Agent, or Firm*—Akerman Senterfitt

(57) ABSTRACT

A method and system for examining biological tissue includes the steps of radiating a tissue region with a plurality of microwave radiation pulses. The microwave pulses are swept across a range of microwave frequencies. In response to the swept frequency microwave pulses, the tissue region emits a plurality of thermoacoustic signals. At least one image of the tissue region is formed from the plurality of thermoacoustic signals. The signals can be ultrawideband signals.

14 Claims, 3 Drawing Sheets

OTHER PUBLICATIONS

National Academy of Sciences, "Executive Summary," Mammography and Beyond: Developing Technologies for the Early Detection of Breast Cancer, http://www.nap.edu, 2003.

Newman, M., "Developing Technologies for Early Detection of Breast Cancer," A Public Workshop Summary, National Academy of Sciences, 2000.

National Academy of Sciences, "Executive Summary," A Review of the Department of Defense's Program for Breast Cancer Research, http://www.nap.edu, 2003.

Cady, B., "Breast Cancer in the Third Millennium," Journal of Surgical Oncology, 77:225-232, 2001.

Hagness et al., "Three-Dimensional FDTD Analysis of a Pulsed Microwave Confocal System for Breast Cancer Detection: Design of an Antenna-Array Element," IEEE Transactions on Antennas and Propagation, 47:783-791, 1999.

Kruger et al. "Thermoacoustic CT of the Breast," 4682-55, OptoSonics, Inc., http://www.optosonics.com, date is not available.

Wang et al., "Microwave-induced acoustic imaging of biological tissues," Rev. Sci. Instrum., 70:3744-3748, 1999.

Ku et al., "Combining Microwave and Ultrasound: Scanning Thermoacoustic Tomography," Proceedings of the 22nd Annual EMBS International Conference, Chicago, IL, 2321-2323, Jul. 23-28, 2000.

Chan et al., "Microwave-Induced Thermoelastic Tissue Imaging," Biomagnetic and Microwave Imaging, IEEE Engineering in Medicine & Biology Society 10th Annual International Conference, 1988.

De Jongh et al., "Design and analysis of new GPR antenna concepts," Delft University of Technology, Faculty of Information Technology and Systems International Research Centre for Telecommunications-transmission and Radar(IRCTR).

Surowiec et al., "Dielectric Properties of Breast Carcinoma and the Surrounding Tissues," IEEE Transactions on Biomedical Engineering, 35:257-263, 1988.

Fear et al., "Confocal microwave imaging for breast tumor detection: application to a hemispherical breast model," IEEE MTT-S Digest, 1759-1762, 2002.

Kruger et al., "Thermoacoustic Computed Tomography of the Breast at 434 MHz," IEEE MTT-S Digest, 591-594, 1999.

Kruger et al., "Thermoacoustic CT with Radio Waves: A Medical Imaging Paradigm," Thermoacoustics CT with Radio Waves, Radiology, 211:275-278, 1999.

Feng et al., "Microwave-induced thermoacoustic tomography: Reconstruction by synthetic aperture," Am. Assoc. Phys. Med., 28:2427-2431, 2001.

Kruger et al., "Breast Cancer in Vivo: Contrast Enhancement with Thermoacoustic CT at 434 MHz-Feasibility Study," Radiology, 216:279-283, 2000.

Xu et al., "Exact Frequency-Domain Reconstruction for Thermoacoustic Tomography-II: Cylindrical Geometry," IEEE Transactions on Medical Imaging, 21:829-833, 2002.

Xu et al., "Exact Frequency-Domain Reconstruction for Thermoacoustic Tomography-I: Planar Geometry," IEEE Transactions on Medical Imaging, 21:823-828, 2002.

Xu et al., "Microwave-induced thermoacoustic tomography using multi-sector scanning," Am. Assoc. Phys. Med., 28:1958-1963, 2001.

Xu et al., "Time-Domain Reconstruction for Thermoacoustic Tomography in a Spherical Geometry," IEEE Transactins on Medical Imaging, 21:814-822, 2002.

Kruger et al. "Thermoacoustic CT of the Breast," 4682-55, OptoSonics, Inc., http://www.optosonics.com.

Hagness et al., "Two-Dimensional FDTD Analysis of a Pulsed Microwave Confocal System for Breast Cancer Detection: Fixed-Focus and Antenna-Array Sensors," IEEE Transactions on Biomedical Engineering, 45:1470-1479, 1998.

Gabriel et al., "The dielectric properties of biological tissues: III. Parametric models for the dielectric spectrum of tissues," Phys. Med. Biol., 41:2271-2293, 1996.

Kruger et al., "Thermoacoustic CT," IEEE MTT-S Digest, WE3D-4:933-936, 2000.

Goscin et al., "Magnetic Resonance Imaging of the Breast," Cancer Control, 8:399-406, 2001.

Kinkel et al., "MR Imaging: Breast Cancer Staging and Screening," Seminars in Surgical Oncology, 20:187-196, 2001.

Waxman, A., "PET:functional imaging applications in oncology," MEDICA/MUNDI, 46:12-18, 2002.

Kaul et al., "Early Detection of Breast Cancer: Is Mammography Enough?," Hospital Physician, www.turner-white.com, 2002.

Gabriel et al., "The dielectric properties of Biological tissues: I. Literature survey," Phys. Med. Biol., 41:2231-2249, 1996.

Gabriel et al., "The dielectric properties of Biological tissues: II. Measurements in the frequency range 10Hz to 20GHz," Phys. Med. Biol., 41:2251-2269, 1996.

Davis, S.K. et al., "Frequency-domain penalized least-squares beamformer design for early detection of breast cancer via microwave imaging," 2002 IEEE Sensor Array & Multichannel Signal Procressing Workshop Proceedings, Piscataway, N.J., pp. 120-124 (Aug. 2002).

* cited by examiner

MULTI-FREQUENCY MICROWAVE-INDUCED THERMOACOUSTIC IMAGING OF BIOLOGICAL TISSUE

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The invention relates to systems and methods for imaging biological tissue, and more particularly thermoacoustic imaging systems and methods using swept frequency electromagnetic waves.

BACKGROUND

Breast cancer is one of the most common types of cancer among women and the main cause of death for middle aged women. Each year, over 180,000 new cases of invasive breast cancer are diagnosed and more than 40,000 women die from the disease in the United States. Early detection is currently the best hope for reducing the death rate of this devastating disease. Mammography typically cannot differentiate benign from malignant disease. Moreover, mammography is significantly less accurate in patients with dense glandular breasts.

Consequently, the results of X-ray mammography may show suspicious areas where no malignancy exists, with up to twenty percent of biopsied growths identified as cancerous by a mammogram being identified as malignancies. Furthermore, radiologists interpreting X-ray mammography imagery can overlook between fifteen and twenty-five percent of cancers. Finally, the very process of X-ray mammography, specifically the use of imaging plates, can cause bruising of the breasts and acts as a disincentive for women to undergo mammography screening.

Other imaging modalities have emerged to augment mammography and improve the accuracy of non-invasive breast cancer diagnosis. Ultrasound is currently used to differentiate breast masses and guide aspirations and biopsies. Magnetic resonance imaging has excellent sensitivity in demonstrating breast cancer but has a low specificity. Nuclear medicine studies have recently emerged that detect the increased metabolic rate and vascularity of breast cancers.

During the past several years, microwave imagery has formed the basis of a new, alternative detection technique for the detection of breast cancer. Whereas in X-ray mammography, high-energy ionizing radiation can be passed through the breast to a photographic plate in order to shadow potential tumors, in microwave detection, an array of antennae affixed to the breast surface can "bounce" non-ionizing microwave radiation off malignant growths whose radiation can be detected by the array. Based upon the characteristics of the "bounce", growths can be detected much in the same way that radar can be used to detect objects at a distance.

Microwave imaging for use in breast cancer detection has been referred to as "breast tumor radar." In a typical implementation, a computer can be coupled to an array of small antennae beaming 6 GHz pulsed microwaves. Since normal breast tissue remains largely transparent to microwave radiation, breast tumors which contain more water than normal breast tissue cause the scattering of the beamed microwaves back toward their source. The antennae can detect the scattered microwaves which can be analyzed to construct a three-dimensional image showing both the location and size of the tumor(s).

In a similar effort to microwave imaging based upon the high relative water content of the tumor, new efforts have been undertaken in the application of both ultrawideband radar technology and confocal optical microscopy. This technique can exploit the dielectric constant contrast between normal breast tissue and malignant tumors at microwave frequencies. Specifically, each element in an antenna array sequentially can illuminate an uncompressed breast with a low-power ultrawideband microwave pulse. Following the acquisition of backscattered waveforms, the array can be synthetically focused by time shifting and adding the recorded returns. A subsequent synthetic scan of the focal point permits the detection of strong scattering sites in the breast which can be identified as malignant tumors.

Microwave-induced thermoacoustic imaging is a microwave imaging technique which has demonstrated tremendous potential for tissue imaging. Thermally-induced acoustic waves can be induced in virtually any material, including biological tissue. More particularly, when tissue becomes heated, the tissue expands in size producing pressure waves, which propagate throughout the tissue in all directions. According to general principles of thermoacoustic physics, the thermally-induced acoustic signal can be compared to the manner in which the tissue is heated as well as the local tissue absorption properties within the irradiated tissue volume.

In operation, microwave-induced thermoacoustic imaging involves the use of a short-pulsed microwave beam for irradiating the biological tissue of the breast. The breast tissue can absorb the microwave energy and, responsive to the absorption of the microwave energy, the breast tissue can emanate thermoacoustic waves through thermoelastic expansion. The thermoacoustic waves can carry the information regarding the microwave energy absorption properties of the breast tissue under irradiation. The different energy absorption properties among the different types of breast tissue permit the construction of a distribution of microwave energy absorption pattern in a homogeneous acoustic medium.

For example, U.S. Pat. No. 6,567,688 to Wang discloses a microwave-induced thermoacoustic system and method for imaging biological tissue. Short microwave pulses irradiate tissue to generate acoustic waves by thermoelastic expansion. The microwave-induced thermoacoustic waves are detected with an ultrasonic transducer or transducer array. Each time-domain signal from the ultrasonic transducer is converted to a one-dimensional image along the acoustic axis of the ultrasonic transducer. Scanning the system perpendicularly to the acoustic axis of the ultrasonic transducer generates multi-dimensional images in real-time without computational image reconstruction. Wang discloses use of a single microwave frequency generally in the range from 300 MHz to 3 GHz.

Although the Wang system provides fairly good quality breast images, the test conditions disclosed were highly oversimplified or not representative as compared to conditions normally present during annual breast imaging. First, the size of the test sample had been comparable to the irradiation aperture of the microwave waveguide so that the test sample was irradiated uniformly and the test sample heated effectively. Second, the samples tested comprising muscle cylinders inserted in the fat were not totally enclosed by skin or even fat. Thus, the experiment did not produce a skin effect and allowed the muscle cylinders to remain under direct irradiation of the microwave pulses.

For human breast imaging, however, the situation can be much more complicated. The human breast is much larger in size, usually has an irregular shape if not compressed, and is covered with about a two millimeter thick skin having dielectric properties significantly different from normal breast tissue. These factors make it much more difficult to heat the breast effectively. Moreover, the breast tissue is far from homogeneous. The breast is composed of lobules of lactiferous glands and ducts set in fat tissue that exit at the nipple. The propagation of the microwave-induced thermoacoustic signals in the regions containing many glandular lobules and ducts will be significantly different as compared to pure fat tissue.

Notably, the propagation paths of the microwave-induced thermoacoustic signals generated from the tumors inside the breast will change due to the refractions at the skin margin. These abnormalities in thermoacoustic wave propagation will introduce approximations into the calculation of the signal back propagation. Due to the slow acoustic wave propagation speed or short wavelength, the errors on the order of millimeters in determining the signal propagation path lengths can degrade the reconstructed image severely. For instance, experiments have shown that the thermoacoustic signals induced at the skin margin and their scatterings from the fat-glandular and fat-duct tissue boundaries are very strong, and the image quality degrades significantly at the depths greater than about forty to forty-five millimeters behind the nipple region. Therefore, the skin not only changes the microwave power deposition pattern in the breast, but also introduces strong clutter.

To enhance the thermoacoustic imaging of the human breast, several efforts have been made to improve the performance of conventional thermoacoustic imaging technology. As an example, to achieve a higher spatial resolution, an array with more transducers or more acoustic data acquisitions at a larger aperture has been considered. Alternatively, for a deeper microwave penetration, an increase of the transmitted microwave power has been an obvious consideration, and an array of multiple waveguides placed radially around the breast has also been suggested. Other reported efforts include searching for a more suitable microwave frequency and a more effective pulse duration of the microwave pulses. In summary, although microwave-induced thermoacoustic imaging has great potential for early breast cancer detection, much work needs to be done toward making microwave-induced thermoacoustic imaging a practical method for early breast cancer screening.

SUMMARY OF THE INVENTION

A method of examining biological tissue includes the steps of radiating a tissue region with a plurality of microwave radiation pulses. The microwave pulses are swept across a range of microwave frequencies. In response to the swept frequency microwave pulses, the irradiated tissue region emits a plurality of thermoacoustic signals. At least one image of the tissue region is formed from the plurality of thermoacoustic signals. The tissue region can comprise breast tissue. A plurality of images from fractional portions of the breast can be taken, and the respective images combined to form an overall image of the breast.

The plurality of radiation pulses can span a frequency range of at least 1 GHz. In a preferred embodiment, the radiation pulses are ultra wideband signals.

The step of forming at least one image can comprise adaptive beamforming. The adaptive beamforming step can include the steps of providing a sensor array including a plurality of sensor elements, wherein an array steering vector corresponding to a signal of interest (SOI) is unknown, representing said array steering vector with an ellipsoidal uncertainty set, bounding a, covariance fitting relation for said array steering vector with said uncertainty ellipsoid, and solving the matrix fitting relation to provide an estimate of the array steering vector.

The pulses can include a plurality of different polarizations. The method can include the, step of pattern recognition from the image obtained. The pattern recognition can comprise adaptive signal processing.

A system for examining biological tissue comprises a microwave radiation source for radiating a tissue-region with a plurality of microwave radiation pulses, the pulses swept across a range of microwave frequencies, wherein the tissue region emits a plurality of thermoacoustic signals responsive to the microwave pulses. The microwave radiation source can be a source of ultra wideband signals. An acoustic transducer array receives the thermoacoustic signals, and provides electrical signals in response thereto. An imager forms at least one image of said tissue region from the electrical signals. A horn antenna, such as a pyramidal horn, a corrugated horn, or a TEM horn, can be coupled to the microwave radiation source for emanating the microwave pulses. The horn arms can be curved to improved the impedance match with the tissue being irradiated.

The system can include a structure for translating at least one of the transducer array and the antenna. The pulses include a plurality of different polarizations, such as by rotating a TEM horn antenna coupled to the microwave generator.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

Figure 1:
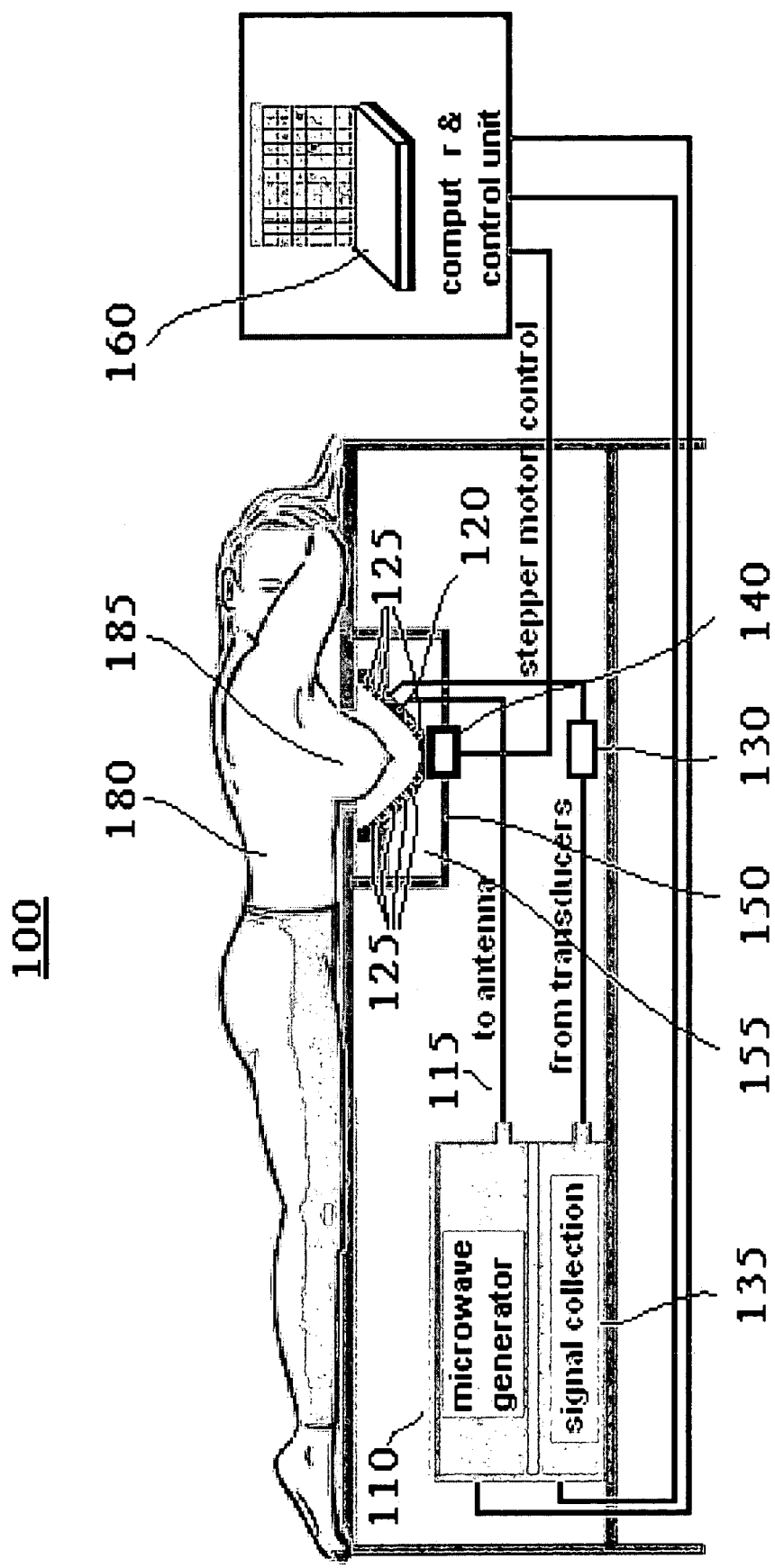
FIG. 1 illustrates a thermoacoustic scanning system according to an embodiment of the invention.

A method of examining biological samples and related system radiates a tissue region with a plurality of short microwave radiation pulses, wherein the plurality of radiation pulses are swept across a range of microwave frequencies. Although the biological sample is generally described herein as being human breast tissue, the systems and methods described herein are suitable for imaging other human tissue regions, and tissues from non-human subjects, such as animals.

A microwave is generally defined as an electromagnetic wave having a wavelength from 300 mm to 10 mm, corresponding to a frequency of 1 GHz to 30 GHz. The microwave frequency generally regarded as a carrier frequency, and the beam is generally defined by the radiation pattern. The microwave pulses are generally in a frequency range from about 1 GHz to 10 GHz to provide sufficient penetration depth into normally lossy biological tissue. The range of microwave frequencies preferably spans a frequency range of at least 1 GHz. For systems according to the invention, the microwave pulse width will generally be on the µs order.

The tissue absorbs the microwave energy and emanates a plurality of thermoacoustic waves due to thermoelastic expansion. The generated acoustic waves carry information about the microwave energy absorption properties of the tissue under irradiation. The different absorption properties among different types of tissue permit the construction of a distribution of microwave energy absorption pattern in a homogeneous acoustic medium. At least one image of the tissue region is formed from the plurality of thermoacoustic signals. In a preferred embodiment of the invention, a plurality of images are taken from a plurality of local regions comprising the breast and combined to form an image of the whole breast.

In contrast to the use of single frequency pulses in earlier work, such as U.S. Pat. No. 6,567,688 to Wang, the microwave pulses used in the present invention are swept across a range of microwave frequencies. Use of frequency sweeping gathers much more information about tissue regions, such as the human breast, as compared to Wang's fixed frequency microwave-induced thermoacoustic imaging. With frequency sweeping according to the invention, the microwave energy deposition patterns of the breast can be obtained as a function of the irradiation microwave frequency. This rich information can be exploited for much better thermoacoustic imaging formation, clutter suppression, and pattern recognition for cancer detection, thus permitting detection of smaller tumors.

According to the thermoacoustic physics, the frequency content of the microwave-induced thermoacoustic pulse is closely related to the way an irradiated object, such as breast tissue, is heated since the microwave pulses at different frequencies will suffer from different dispersive effects due to the frequency-dependent dielectric properties of the breast tissue. For example, the transmitted power level, the transmitted pulse duration and pulse repetition frequency for each irradiation microwave frequency can all be controlled and adjusted for improved cancer detection.

These microwave parameters can be controlled at the generator, such as using a function generator to modulate the microwave generator. For improved cancer detection using systems according to the invention, irradiation of the target biological tissue (e.g. tumor) is performed at microwave frequencies lower than about 10 GHz. Higher transmitted power level within the American National Standards Institute (ANSI) restrictions and a higher duty cycle will also generally improve performance. It is noted that the selected pulse parameters will generally be different at different microwave frequencies, because different propagation attenuation will occur at different microwave frequencies due to the frequency-dependent tissue dielectric parameters.

There is a wide range of microwave absorption coefficients among various tissue in the human breast. This range provides the potential for high imaging contrast for the breast. The microwave induced thermoacoustic signals propagate throughout the breast in all directions at approximately 1.5 mm/µs. Because of this low propagation velocity of acoustic waves in soft tissue, thermoacoustic signals with MHz bandwidth can provide-millimeter range spatial resolution. This very fine resolution is much higher than that of X-ray mammography, and hence is much more suitable for detection of tiny tumors or early stage breast cancer detection.

It has been shown that most breast cancers, estimated at approximately 80%, occur in the ductal region, while the remaining 20% seem to originate in the lobules. Almost 50% of all breast tumors occur in the quadrant, near the armpit where the breast is less than about 2.5 cm deep. The depth of a typical normal, non-lactating human breast is on the order of 5 cm. Therefore, the penetration depth for breast tumor stimulation should be on the order of 5 cm. Although theoretically the stimulating radiation used to induce thermoacoustic waves from the irradiated tissue may generally lie anywhere in the electromagnetic spectrum, for effective thermal induction, the penetration depth of the stimulating irradiation must be sufficient. It has been found that ultraviolet, optical or infrared radiation does not provide stimulation to the required depth for breast cancer detection and is accordingly not generally suitable for use with thermoacoustic imaging.

As noted above, there is a wide selection of potential frequencies at which the microwaves can penetrate at least several centimeters into the tissue, such as from 1 GHz to about 10 GHz. Operation at even higher frequencies allows use of a relatively smaller system volume, due to the corresponding shorter wavelength. However, although the dielectric contrast between normal and cancerous breast issue is significant for microwave frequencies up to 20 GHz, beyond about 10 GHz, the microwave penetration depth into breast tissue decreases significantly. Frequencies below 1 GHz can also be considered, such as the lower UHF (e.g., 433 MHz). However, using UHF radiation, the system will take on a larger volume, and local irradiation will generally becomes substantially more difficult.

The microwave penetration depth in the tissue depends on the fundamental properties of breast tissue at the particular microwave frequency. Quite different from the interaction mechanism for infrared, optical and X-rays, microwaves interact with the biological tissue primarily according to the water content of the tissue. Different water content in tissue results in different dielectric properties of the tissue, for example, different dielectric permittivity (or relative permittivity $\epsilon_r$) and conductivity ($\sigma$) for microwaves. Permittivity is also referred to as the dielectric constant. High permittivity is generally associated with high conductivity ($\sigma$). However, for breast tissue, both the permittivity and conductivity are functions of frequency, so that at higher frequency, the permittivity becomes smaller while the conductivity becomes larger. The higher the conductivity of the tissue, the higher the microwave attenuation as the wave propagates in the tissue.

Due to the different water content in the normal breast tissue (high-fat, low-water, low- salt) and the malignant tumor (low-fat, high-water, high-salt), the microwave energy absorbed by the tumor and normal breast tissue will be significantly different. From about 10 MHz to about 20 GHz, tissue energy absorption is predominantly a function of the bound-water content of the tissue. The higher the bound-water content, the higher the absorption.

A number of studies have demonstrated that the dielectric properties of the high-bound-water-content cancerous tissue are somewhat like those of the muscle, which has been known to have dielectric properties significantly different from those of the normal low-bound-water-content fatty tissue. Dielectric properties of breast carcinoma at specific radiowave and microwave frequency bands have been measured and have demonstrated that malignant tissue has a dielectric constant significantly higher than that of normal breast tissue.

For the tissue dielectric parameters, the microwave attenuation in the normal breast tissue is less than 4 dB/cm for frequencies up to 10 GHz. Hence for frequencies up to 10 GHz, sufficient penetration into the breast is possible to heat a potential tumor in the tissue. Microwave tissue heating is very safe since the tissue temperature rises only a small fraction of a degree centigrade on average.

In a preferred embodiment, the radiation pulses are "ultra-wideband" signals. However, the invention is in no way limited to ultrawideband signals. Ultrawideband technology (UWB) is sometimes referred to as impulse radio which is one of its most common forms. UWB signals have also come to signify a number of other terms, such as impulse, carrier-free, baseband, time domain, nonsinusoidal, orthogonal function and large-relative-bandwidth radio/radar signals. As used herein, the term "UWB" includes all of these.

Ultrawideband (UWB) systems transmit signals across a much wider frequency than conventional systems. The bandwidth of a UWB signal is generally at least 25% of the center frequency. Thus, a UWB signal centered at 2.4 GHz would have a minimum bandwidth of 600 MHz and the minimum bandwidth of a UWB signal centered at 4 GHz would be about 1 GHz. The most common technique for generating a UWB signal is to transmit pulses with durations less than about 1 nanosecond. UWB wireless technology provides very low power consumption (microwatts), virtual immunity from RF noise that makes it well suited for use with this invention.

UWB is believed by many to have been first fully described in a series of patents including U.S. Pat. No. 4,641,317 and U.S. Pat. No. 5,363,108 to Larry W. Fullerton. A second generation of Fullerton UWB patents include U.S. Pat. Nos. 5,677,927, 5,687,169, 6,031,862.

Because of microwave attenuation in the breast tissue, it might appear that the intensities of the microwave-induced thermoacoustic signals would be far weaker than the ultrasonic pulse induced reflections provided by conventional ultrasound imaging. However, a unique advantage of microwave-induced thermoacoustic, imaging is that the inhomogeneous microwave energy absorption property of the tissue can be detected in the thermoacoustic signal even when the acoustic property of the tissue is homogeneous. According to microwave-induced thermoacoustic theory, the induced ultrasound signal is proportional to the temperature increment in the tumor, the temperature increment is proportional to the absorbed microwave power in the tumor, and the absorbed microwave power is proportional to the square of the microwave field strength (the signal strength).

In a preferred embodiment of the invention, adaptive signal processing algorithms are used to provide improved spatial resolution and significantly less clutter from the received thermoacoustic signal. Advanced pattern recognition methods are also preferably provided for more accurate cancer detection and cancerous and benign tumor classification.

FIG. 1 illustrates a thermoacoustic scanning system 100 according to an exemplary embodiment of the invention. The patient 180 is oriented in a prone position. System 100 is both safe and comfortable and avoids the ionizing radiation and breast compression associated with conventional X-ray mammography.

The system 100 includes microwave radiation generator 110, such as an ultrawideband microwave pulse generator. Microwave transmission lines 115, such as coaxial lines, guide the microwave pulses provided by generator 110 to an antenna 120 for emission to illuminate a local breast area. Antenna 120 will generally be a single antenna as shown in FIG. 1. Although not shown in FIG. 1, antenna 120 can be embodied as an antenna array (not shown) which can generally be used to provide improved illumination and irradiation efficiency over a single antenna embodiment. For example, the antenna array design can be similar to the energy-focused array used in the Geo-Cenfer's GPR. However, the array design and required control electronics will add significant complexity to the system.

A commercially available microwave generator can be used as generator 110, with its output power, frequency and pulse duration adjustable and controllable by a computer 160. However, the output power of a conventional commercially available (pulsed) microwave generator may be much lower than the power needed, which is generally about 10 to 20 W to induce the thermoacoustic signal. To increase the irradiation power of the system, a power amplifier (not shown) can amplify the signal provided by microwave generator 110.

Antenna 120 is preferably an ultra wideband antenna when generator 110 is an ultrawideband microwave pulse generator. Non-dispersive antennas, such as the bow-ties, TEM horns, pyramidal horns, a corrugated horns, or other resistively-loaded monopoles as well as dipole antennas, are preferred since they may be designed to achieve high radiation efficiency with relatively small size. These antenna are designed to support a traveling Wave so that the signal is being radiated while it is traveling along the antenna structure. Therefore, the non-dispersive antennas can be used for transmitted pulse shape control since these antennas do not significantly broaden the pulse shape upon transmission and are preferred for pulsed radiation. Once the pulse is transmitted by antenna 120, the frequency response of the antenna 120 causes the pulse to resonate at the antenna center frequency, with the pulse width equal to the inverse of the antenna bandwidth. To maintain the desired pulse shape and minimize the reflections from the antenna end, the shapes of the antenna arms and the resistance distributions on the antenna structure is preferably designed to minimize the reflection from the antenna ends.

The breast can be viewed as a load to the radiating antenna. In one embodiment, a horn antenna with curved antenna arms is used. The resistance distributions on the antenna arms are used to absorb the reflected waves along the arms. The lens will also provide better impedance match between the horn and the breast (load) to further reduce further the reflection at the arm ends.

Antenna 120 is generally unbalanced, while the transmission line, such as a coaxial feed line, is generally balanced. Thus, impedance matching can provide improved transmission efficiency and minimizes signal ringing. In a preferred embodiment of the invention, a balun (not shown) is provided between the transmission line which delivers the microwave pulses and the antenna 120 to provide an impedance match. In the case of an antenna array (not shown), a single balun can be used provided the respective antenna elements are substantially identical.

A stepper motor 140 controls the position of imaging tank 150, which in turn controls the position of antenna 120 and acoustic transducer array 125. The antenna 120 will provide local irradiation and the transducer array 125 will collect data according to the requirement of data processing imaging. In general, the requirement can be met by rotating the transducer array 125 using small steps in this arrangement, the stepper motor 140 drives the transducer array 125. Only after all the necessary acoustic data collection at one local breast area is completed, stepper motor 140 will translate transducer array 125 to the next local area.

Acoustic transducer array 125, such as a piezoelectric based transducer array 125, can be used to collect the thermoacoustic signals generated by the irradiated tissue. Transducer array 125 is selected to meet the system requirements for data acquisition and data processing. A plastic cone support (not shown) is preferably provided for the transducer array 125. The signals are preferably amplified by signal amplifiers, 130 and then sent to signal collection unit 135.

Imaging tank 150 has a coupling medium 155 therein. Thus, the breast 185 of the patient 180, irradiating antenna 120 and transducer array 125 are all surrounded by the coupling medium 155. The coupling medium 155 should have dielectric properties that give the best microwave match between lenses (not shown in FIG. 1) of the antenna 120 and skin of breast 185. Meanwhile, its acoustic properties should give the best acoustic match between the transducer array 125 and the normal breast tissue. Such a coupling 155 medium is needed for effective microwave irradiation. Acoustic matching also allows for the accurate determination of the propagation paths of the microwave-induced thermoacoustic waves.

Precise propagation path determination is needed because the typical wavelength of the thermoacoustic wave at 1 MHz is 1.5 mm in the breast tissue while the breast skin is 2 mm thick. If the acoustic properties of the coupling medium are the same as those of the normal breast tissue, the acoustic wave will propagate at the same speed in the coupling medium as in the normal breast tissue beneath the skin. For example, mineral oil can be used as a coupling medium. As a result, the thermoacoustic signal will propagate in parallel before and after it crosses the skin and the skin effect can be accurately calculated and compensated out.

A computer 160, such as a laptop computer, provides control of signal collection unit 135 and stepper motor 140. Computer 160 performs signal processing of data stored at signal collection unit 135 and displays images compiled.

Figure 2:
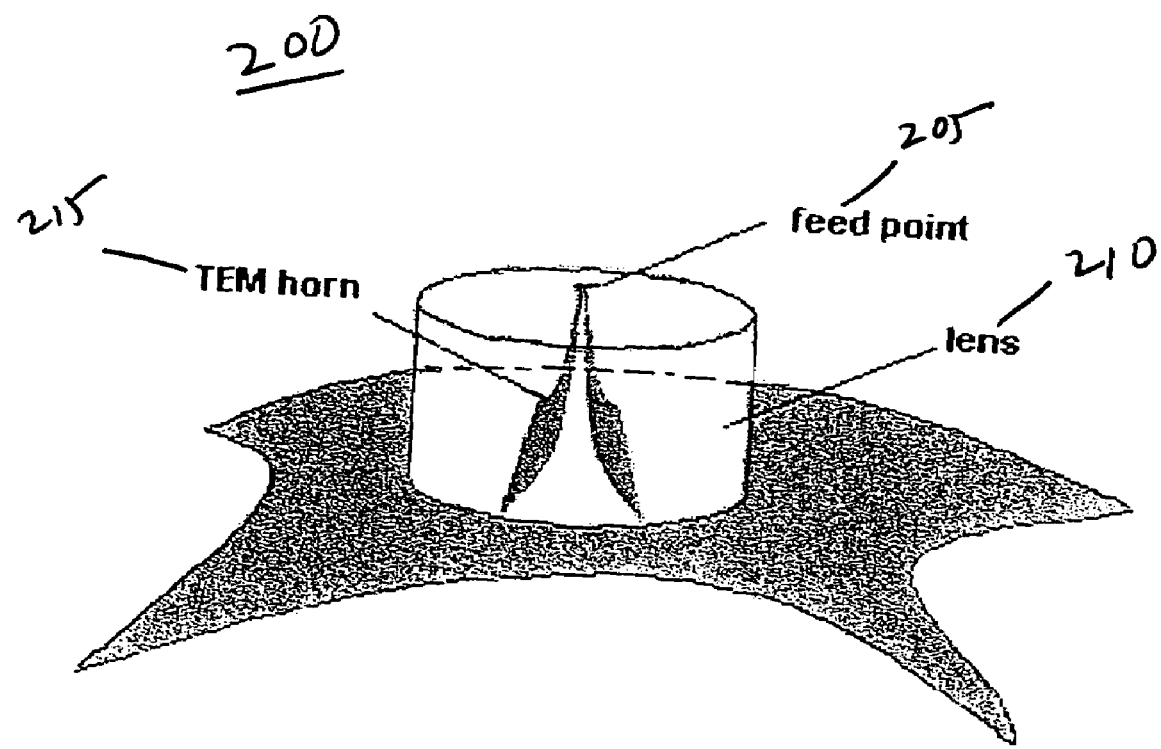
FIG. 2 shows a lensed TEM horn antenna upon which an antenna array can be based for thermoacoustic scanning using ultrawideband irradiation of the breast.

FIG. 2 shows a lensed TEM horn antenna 200 upon which antenna 120 can be based for effective ultrawideband irradiation of biological tissue, such as the breast. A TEM horn antenna is a typical ultrawideband antenna, which can provide a satisfactory UWB irradiation pattern for breast imaging. Antenna 200 includes TEM horn 215 and a feed point 205 for receiving a UWB signal from a microwave generator (not shown) via a suitable microwave transmission line (not shown). Antenna 200 also includes a lens 210 which surrounds TEM horn 215 and focuses the radiated beam, reduces the size of the antenna 200, maintains an effective radiation aperture, and minimize the microwave reflections.

For efficient microwave irradiation, the antenna can be designed to achieve desired parameters, such as polarization, radiation pattern, gain, and beam width. For example, antenna polarization can play an important role in tumor heating. Antenna design software can be used for initial antenna design parameters based on the desired antenna parameters. Testing of the design generally follows, followed by one or more design and test iterations until the desired parameters are achieved.

Cancerous tumors are generally non-spherical in shape. Accordingly, the thermoacoustic signals emitting by such tumors are generally polarization sensitive. In one embodiment of the invention, the invention exploits the polarization sensitivity of tumors by using multiple polarization microwave pulses. For example, in general, TEM horn antennas provide linear polarization normal its two metal triangular plate (arms) in the horn aperture. If such a TEM horn antenna is used, multiple polarizations can be achieved simply by rotating the TEM horn antenna.

It is preferred to irradiate one section of the breast at a time since a local breast survey with a low microwave power will allow for local thermoacoustic data acquisition. To survey the entire breast at one time, a common way is to illuminate and heat the entire breast at the same time. Such heating induces strong thermoacoustic signals from the entire skin of the breast since the skin of the entire breast is heated, which can lead to the presence of strong clutter in the thermoacoustic images.

In contrast, a local survey according to the invention allows for low microwave power transmission and hence results in reduced clutter due to only a small portion of the breast skin being heated. To radiate small breast region, the antenna should have a narrower beam width and should be put in close proximity to the breast, such, as 2 to 3 cm, or less, to the breast section under interrogation. A local survey also allows both the microwave irradiation antenna and the acoustic transducer array being in close proximity. Close proximity allows for better irradiation within the breast for the same transmission power. The received thermoacoustic signals are also stronger and their propagation paths can be calculated more accurately when a local survey is used.

Through adaptive signal processing, the already reduced clutter caused by the skin effect provided by local heating according to the invention can be adaptively suppressed and the spatial resolution can thus be substantially improved. Finally, the 3-D images of the entire breast can be obtained by fusing the 3-D localized images obtained through a plurality of local surveys.

Improved signal processing can also improve imaging results. The image formation methods used by U.S. Pat. No. 6,567,688 to Wang is an example of a data-independent delay-and-sum (with or without weighting) approach. These approaches tend to have poor resolution (relative to the best possible resolution a transducer array can offer) and high sidelobe problems, especially when the transducer array is not composed of uniformly and linearly spaced transducers, which is generally the case for the microwave-induced TAI systems. For uniform linear arrays, data-independent weight vectors, such as the Taylor widow, can be used to reduce the peak sidelobe level at the cost of poorer resolution. For other arrays, however, there are no effective ways to achieve desired sidelobe controls. Yet in array processing, sidelobe control is essential for clutter suppression. With high peak sidelobe levels, the energies of the strong thermoacoustic signals such as those due to the breast skin are scattered all over the thermoacoustic image through the sidelobes.

In a preferred embodiment, adaptive beamforming is used for thermoacoustic image formation since the adaptive approaches are ideally suited for a ultrawideband stepped frequency thermoacoustic imaging system according to the invention due to the large amount of information gathered by the system. The adaptive beamforming approaches can have much better resolution and much better interference rejection capability, which means much lower peak sidelobe levels and hence much better clutter suppression, than data-independent beamformers.

The standard Capon beamformer (SCB) has better resolution and much better interference rejection capability than data-independent beamformers, provided that the steering vector of the transducer array corresponding to each pixel of the image is accurately known. However, there are many factors in microwave-induced thermoacoustic imaging that can degrade the performance of SCB, including array calibration errors due to imprecise knowledge of the transducer responses and transducer position uncertainties and the uncertainties of the thermoacoustic signal propagation path calculations. Whenever this happens, the performance of SCB may become worse than that of the data-independent beamformers, such as the delay-and-sum beamformer. To account for the array steering vector errors, additional linear constraints, including point and derivative constraints, can be imposed to improve the robustness of SCB. However, these constraints are not explicitly related to the uncertainty of the array steering vector. Moreover, for every additional linear constraint imposed, the beamformer loses one degree of freedom for clutter suppression. Diagonal loading (including its extended versions) has been a popular approach to improve the robustness of SCB. However, for most of these methods, it is not clear how to choose the diagonal loading level based on the uncertainty of the array steering vector.

An improved Capon beamformer method referred to as a robust Capon beamformer (RCB) is described in copending and commonly assigned U.S. patent application Ser. No. 10/358,597 entitled "Robust Capon Beamforming" published as U.S. Published Application No. 2004/0150558 A1 on Aug. 5, 2004 by the same inventors as the current application. U.S. application Ser. No. 10/358,597 is hereby incorporated by reference into the current application in its entirety. The method described therein includes the steps of providing a sensor array including a plurality of sensor elements, wherein an array steering vector corresponding to a signal of interest (SOI) is unknown. The array steering vector is represented by an ellipsoidal uncertainty set. A covariance fitting relation for the array steering vector is bounded with the uncertainty ellipsoid. The matrix fitting relation is solved to provide an estimate of the array steering vector. The RCB provides a simple way of eliminating the scaling ambiguity when estimating the power of the desired signal.

Figure 3:
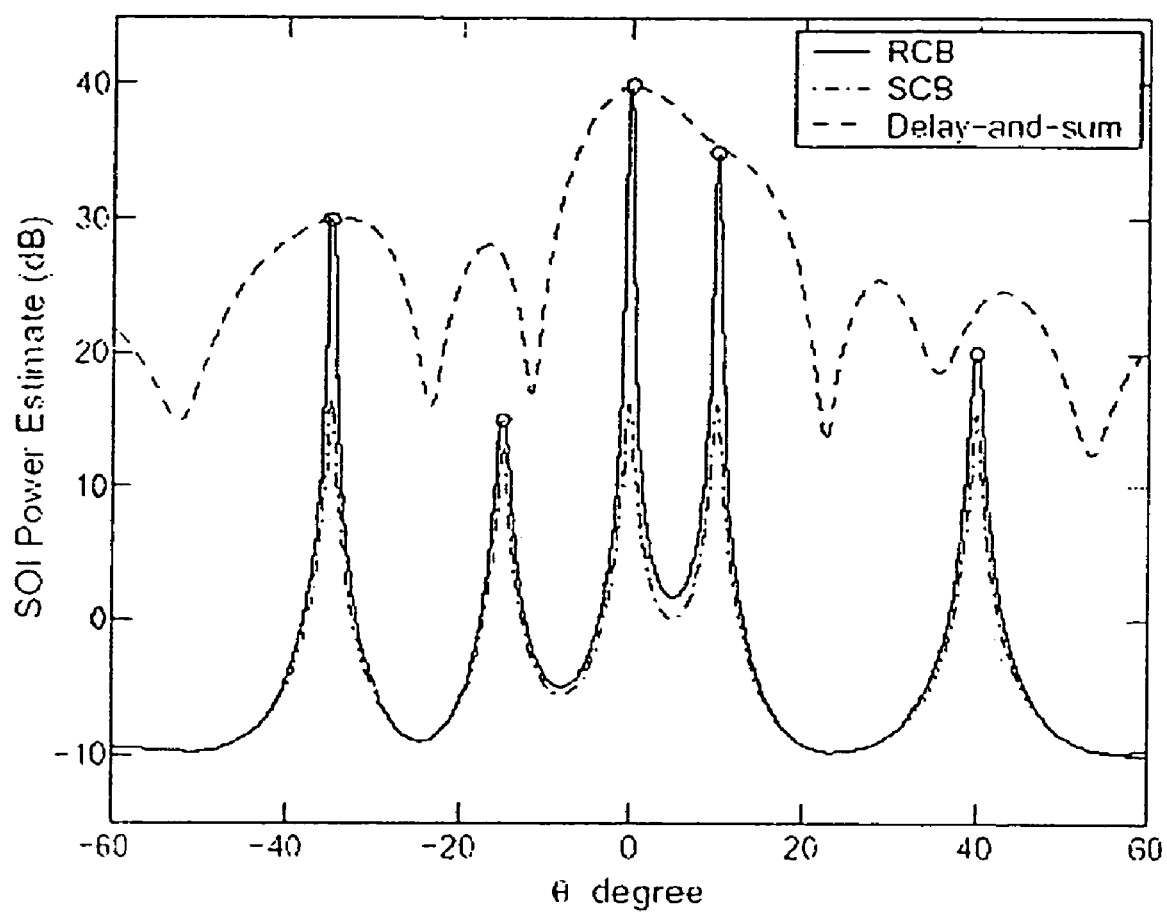
FIG. 3 shows power estimates vs. the steering vector direction for three (3) different types of adaptive beamformer approaches.

To demonstrate the potential benefit of RCB for thermoacoustic imaging according to the invention, as compared to SCB and the data-independent delay and-sum beamformer, FIG. 3 provides some comparative data. Five plane waves from different spatial angles and with different powers (as indicated by the circles) impinge on a uniform linear array with ten sensors. The data-independent approach has much poorer resolution (peaks almost 15 times wider than those of RCB, inability to resolve two closely spaced signals) and much higher sidelobe levels (peaks when there is no signal, incorrect power estimates for weak signals) than the data-adaptive approaches. The RCB approach provides much more accurate signal power estimation (which means excellent interference rejection capability since all five signals interfere with each other) than the SCB method since the latter approach may suppress the signal of interest as interference in the presence of steering vector errors.

Application specific factors for thermoacoustic imaging according to the invention require extending the RCB algorithm to wideband signals. As disclosed in U.S. application Ser. No. 10/358,597, the RCB algorithm is generally described for narrowband signal. To extend the RCB for application to wideband signals, a wideband signal can be divided into several narrowband frequency bins, and the RCB applied to each bin. Thus, the relatively wideband thermoacoustic signal can be treated as comprising a plurality of narrow pulses with the arrival time and pulse duration approximately known. Through time gating, a large portion of signal interferences can be removed before applying the RCB.

Pattern recognition techniques can also improve early breast cancer detection due to the small size of the cancerous tumor and the existence of the residue clutter and other disturbances. By using intelligent joint time-frequency analysis as well as pattern recognition techniques, including the data dimension reduction approach of the joint use of Fisher's discriminant criterion and principal component analysis as well as the training method of linear discriminant analysis, pattern detection can be improved significantly.

Pattern recognition for early breast cancer detection can look for the unique features special to the cancerous tumors such as time-frequency characteristics, which are available through using ultra wideband stepped frequency microwave-induced thermoacoustic imaging systems according to the invention, such as system 100. Wavelet packet transforms can be used to extract features on the tumors efficiently. The features can be analyzed by machine learning algorithms to determine if it cancer is present.

Since the breast cancer screening should be performed regularly, the thermoacoustic images from previous imagings (e.g. from the prior year) can be stored in a suitable computer and used as a baseline for change detection. Change detection is a concept exploited in airborne radar signal processing, such as to locate targets hiding next to a tree. Using the invention, the combination of pattern recognition and change detection can be an effective tool for the detection of otherwise undetectable malignant tumors at the earliest stages.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A method of examining biological tissue, comprising the steps of:
    radiating a tissue region with a plurality of microwave radiation pulses, said plurality of radiation pulses spanning a range of microwave frequencies of at least 600 MHz, wherein said tissue region emits a plurality of thermoacoustic signals responsive to said plurality of microwave pulses, and
    forming at least one image of said tissue region from said plurality of thermoacoustic signals,
    wherein said step of forming at least one image comprises adaptive beamforming.

2. The method of claim 1 wherein said tissue region comprises breast tissue.

3. The method of claim 2, wherein said at least one image of said breast tissue comprises a plurality of said images, said plurality of images from fractional portions of said breast, further comprising the step of combining said images from said local regions to form an overall image of said breast.

4. The method of claim 1, wherein said frequency range is at least 1 GHz.

5. The method of claim 1, wherein said step of forming at least one image comprises adaptive beamforming.

6. The method of claim 5, wherein said adaptive beamforming comprises the steps of:
providing a sensor array including a plurality of sensor elements, wherein an array steering vector corresponding to a signal of interest (SOI) is unknown;
representing said array steering vector with an ellipsoidal uncertainty set;
bounding a covariance fining relation for said array steering vector with said uncertainty ellipsoid, and
solving said covariance fitting relation to provide an estimate of said array steering vector.

7. The method of claim 1, wherein said pulses include at plurality of different polarizations.

8. The method of claim 1, further comprising the step of pattern recognition from said image.

9. The method of claim 8, wherein said step of pattern recognition comprises adaptive signal processing.

10. A system for examining biological tissue, comprising:
a microwave radiation source for radiating a tissue region with a plurality of microwave radiation pulses, said plurality of radiation pulses spanning a range of microwave frequencies of at least 600 MHz, wherein said tissue region emits a plurality of thermoacoustic signals responsive to said microwave pulses;
an acoustic transducer array for receiving said thermoacoustic signals, said transducer array providing electrical signals in response thereto, and
an imager comprising a signal processor having an executable adaptive beamforming algorithm,
said algorithm forming at least one image of said tissue region from said electrical signals.

11. The system of claim 10, further comprising at least one horn antenna coupled to said microwave radiation source for emanating said plurality of microwave pulses.

12. The system of claim 11, further comprising structure for translating at least one of said transducer array and said antenna.

13. The system of claim 10, wherein said plurality of radiation pulses span a frequency range of at least 1 GHz.

14. The system of claim 10, wherein said pulses include a plurality of different polarizations.

* * * * *